(12) United States Patent
Horton et al.

(10) Patent No.: US 7,148,488 B2
(45) Date of Patent: Dec. 12, 2006

(54) APPARATUS FOR MEASURING RADIATION AND METHOD OF USE

(75) Inventors: Keith Horton, Honolulu, HI (US); John Porter, Honolulu, HI (US); Peter Mouginis-Mark, Honolulu, HI (US); Clive Oppenheimer, Cambridge (GB); Harold Garbeil, Kailua, HI (US)

(73) Assignee: University of Hawaii, Honolulu, HI (US)

( * ) Notice: Subject to any disclaimer, the term of this patent is extended or adjusted under 35 U.S.C. 154(b) by 139 days.

(21) Appl. No.: 10/461,860

(22) Filed: Jun. 13, 2003

(65) Prior Publication Data
US 2004/0036027 A1   Feb. 26, 2004

Related U.S. Application Data

(60) Provisional application No. 60/388,764, filed on Jun. 13, 2002.

(51) Int. Cl.
*G01N 21/33* (2006.01)

(52) U.S. Cl. .................................. 250/372; 356/326

(58) Field of Classification Search ............ 250/372, 250/373, 339.11, 339.13, 343, 345, 338.5; 356/326
See application file for complete search history.

(56) References Cited

U.S. PATENT DOCUMENTS

| | | | | |
|---|---|---|---|---|
| 3,944,834 A * | 3/1976 | Chuan et al. ............... 250/372 |
| 4,531,399 A * | 7/1985 | Aono ........................ 73/1.59 |
| 4,795,253 A * | 1/1989 | Sandridge et al. ............ 356/51 |
| 4,853,543 A * | 8/1989 | Ozdemir ..................... 250/372 |
| 4,999,498 A * | 3/1991 | Hunt et al. ............... 250/338.5 |
| 5,060,505 A * | 10/1991 | Tury et al. .................. 250/343 |
| 5,528,363 A * | 6/1996 | Fachinger et al. .......... 356/326 |
| 5,807,750 A * | 9/1998 | Baum et al. ................ 436/164 |
| 5,811,812 A * | 9/1998 | Williams et al. ............ 250/343 |
| 5,835,230 A * | 11/1998 | McAndrew et al. ........ 356/437 |
| 6,154,284 A * | 11/2000 | McAndrew et al. ........ 356/437 |
| 6,287,519 B1 * | 9/2001 | Nordman et al. ............. 422/94 |
| 6,396,056 B1 * | 5/2002 | Lord et al. ............... 250/252.1 |
| 6,509,566 B1 * | 1/2003 | Wamsley et al. ......... 250/338.5 |
| 7,067,818 B1 * | 6/2006 | Harrison ..................... 250/372 |
| 2001/0055118 A1 * | 12/2001 | Nawracala .................. 356/451 |
| 2004/0211900 A1 * | 10/2004 | Johnson ................... 250/338.5 |

* cited by examiner

*Primary Examiner*—David Porta
*Assistant Examiner*—Faye Boosalis
(74) *Attorney, Agent, or Firm*—Duane Morris LLP

(57) ABSTRACT

A device for measuring radiation is disclosed. The device comprises optics and electronics at least partially enclosed in a housing portable by a single human being. In a preferred embodiment, the housing comprises a window to admit radiation of a desired wave length and houses optics and electronics to collect and convert admitted radiation into an electrical signal. A data processor may be disposed in the housing or exterior to the housing and may convert and store the electrical signal into an analyzed, e.g. digital, form. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

23 Claims, 4 Drawing Sheets

APPARATUS FOR MEASURING RADIATION AND METHOD OF USE

RELATION TO OTHER APPLICATIONS

The present application claims priority from U.S. Provisional Application 60/388,764, filed Jun. 13, 2002.

FIELD OF INVENTION

The present invention relates to devices useful to measure radiation, e.g. wavelengths related to a desired target gas.

BACKGROUND OF THE INVENTION

Radiation measurement devices may be used for a variety of measurement services, e.g. analyzing gas species present in a target atmosphere such as for pollution studies, volcano studies, and the like.

Currently, many such devices are either cumbersome to use, given their size and/or weight, or do no provide real time measurements of one or more gas species of interest. Some devices, e.g. an ultraviolet correlation spectrometer developed by Baringer Research of Canada, have been around since the 1960s. Such real time measurements are of interest to remote data gathering. Portability, i.e. the ability to be carried by a single human, is also of interest to remote data gathering such as at remote volcanic and/or oceanic sites.

These devices are typically large, heavy, and expensive instruments, not well suited for deployment in often rugged field environments such as around active volcanoes.

DETAILED DESCRIPTION OF A PREFERRED EMBODIMENT

As used herein, "data" is understood to mean both the singular and the plural. Further, that which is described herein as accomplishable by software may be equivalently accomplished by hardware. Further still, "radiation" is used herein in a broad sense and comprises visible and non-visible light.

Figure 1:
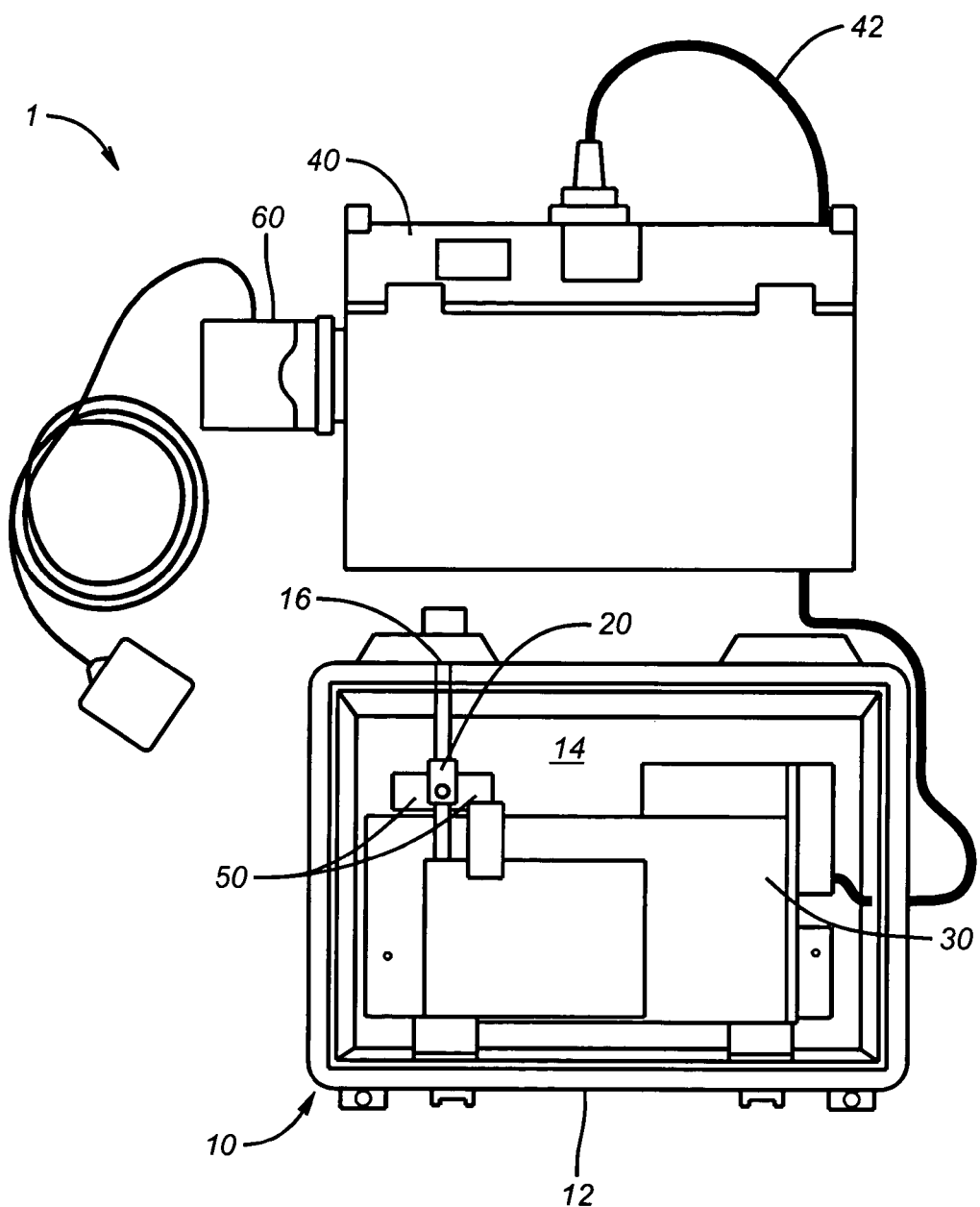
FIG. 1 is a plan overview of an exemplary configuration.
Figure 2:
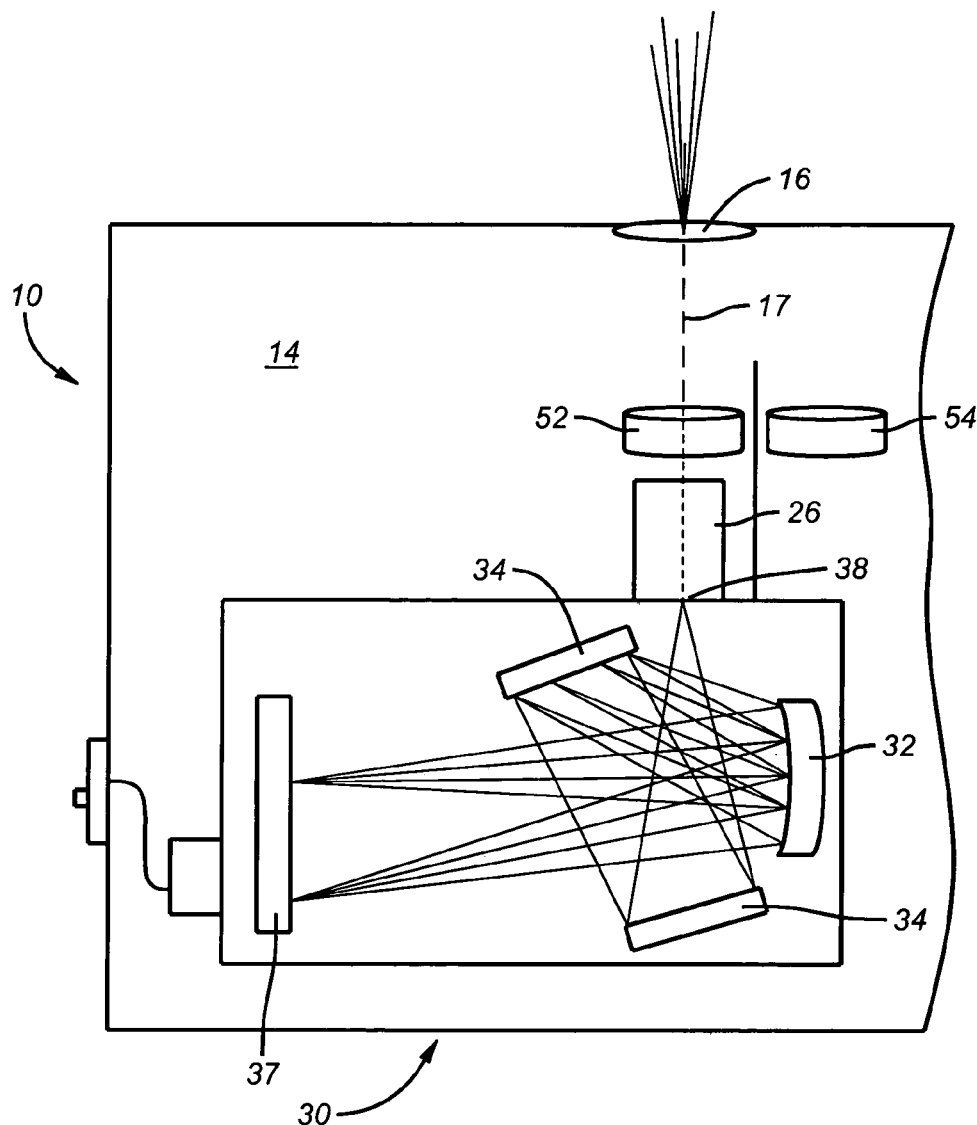
FIG. 2 is a schematic of an exemplary optical portion of an exemplary configuration.

Referring now to FIG. 1 and FIG. 2, device 1 is useful for analyzing a gas, e.g. an atmospheric gas. Device 1 comprises housing 10 adapted to be carried by a human being; optics 20 that are responsive to a known range of radiation disposed at least partially within housing 10; radiation measurement device 30 disposed at least partially within housing 10 and operatively in communication with optics 20; and data processor 40 operatively in communication with radiation measurement device 30. The total weight of device 1 may be around 2 kg, making device 1 suitable for transport and use by a single human being.

Housing 10 is adapted to be carried or otherwise ported by a single human. In a preferred embodiment, housing 10 further comprises shell 12 which is approximately 89 mm by 64 mm by 34 mm in size and which weighs around 200 g. Housing 10 may comprise a durable material. A Pelican® case manufactured by Pelican Products, Inc. of Torrance, Calif. is an example of a suitable housing 10. Shell 12 comprises exterior surface 13 (not shown in the figures) and interior 14. Padding 15 (not shown in the figures) is disposed within interior 14 of shell 12 and is adapted to shield components disposed within interior 14, e.g. from physical shock, harsh environments, and the like.

Housing 10 further comprises window 16 at least partially defining a field of view for optics 20. Window 16 may further comprise a band-pass material for a predetermined wave length range. Pathway 17 (FIG. 2) provides a pathway for radiation which enters via window 16 to continue into interior 14.

Although radiation measurement device 30 may accept an optical fiber input, e.g. from window 16, in a preferred embodiment optics 20 comprises a "telescope," further comprising fiber optic collimating lens 26 (FIG. 2) mounted directly or in close proximity to input aperture 38 (FIG. 2) in radiation measurement device 30. Fiber optic collimating lens 26 may be a fused-silica fiber optic collimating lens with a female SMA connection which may be mated to a male SMA optical input of radiation measurement device 30. In a preferred embodiment, the "telescope" has a focal length of around 42 mm. Fiber optic collimating lens 26, in combination with window 16 may result in a field of view of approximately 2.5° (44 mrad).

In a preferred embodiment, radiation measurement device 30 is a spectrometer which further comprises charge coupled device 37 (FIG. 2) which is responsive to wave lengths of a predetermined range. A USB2000 miniature ultraviolet spectrometer from Ocean Optics, Inc. of Dunedin, Fla. is one such radiation measurement device 30 suitable for use. A StellarNet EPP2000 grating fiber optic spectrometer, manufactured by StellarNet, Inc. of Tampa, Fla. is another. In an exemplary embodiment, charge coupled device 37 comprises a 2048 element charge coupled device arranged as a linear silicon array and coated with a coating to optimize detection of radiation within a target range, e.g. UV in the range of 177–333 nm. In an embodiment, charge coupled device 37 has a 2400 lines mm-1 plane grating, which, combined with a 25 µm slit, results in an optical resolution of 0.25 nm over a wavelength range of 177–330 nm with a sampling resolution of 0.1 nm across the array. For measuring $SO_2$, the entire spectrum in this range may be sampled and stored. For the purposes of measuring SO2 in real-time, a total of 8–9 absorption peaks and troughs between 304 and 320 nm may be analyzed.

Radiation measurement device 30 may further comprise mirror 32 (FIG. 2) disposed in pathway 17 to redirect radiation entering via window 16. Diffraction grating 34 (FIG. 2) may further be disposed intermediate mirror 32 and radiation measurement device 30.

Calibration cell 50 may be present and disposed at least partially within housing 10 and operatively in communication with radiation measurement device 30. In a preferred embodiment, calibration cell 50 further comprises quartz gas high calibration cell 52 (FIG. 2) having a first known concentration of a target gas of interest, e.g. $SO_2$, and quartz gas low calibration cell 54 (FIG. 2) having a second known concentration the gas. For example, high calibration cell 52 may have a gas concentration of around 1400 ppm*m and low calibration cell 54 may have a gas concentration of around 400 ppm*m of $SO_2$. Fused-silica gas cells manufactured by Resonance Ltd. of Ontario, Canada are suitable for use as calibration cells 50.

However, with the addition of multiple gas calibration cells 50, e.g. other UV absorbing gas calibration cells 50, and selection of appropriate spectral peaks or curve fitting, it is possible to simultaneously measure multiple gases.

Additionally, a filter may be present to cooperate with fiber optic collimating lens 26 and window 16. The filter and housing 10 may also reduce the amount of stray light reaching radiation measurement device 30.

Device 1 may be calibrated, e.g. radiation detection device 30 may be calibrated by rotating calibration cell 50 which comprises a known concentration of a gas of interest into the path of radiation, allowing radiation to pass through calibration cell 50 to optical device 30, and adjusting an analyzed value obtained using optical device 30 to correspond to the known concentration of calibration cell 50. The analyzed value may be initialized by obtaining a measurement of calibration cell 50, obtaining a measurement of clean air, and obtaining measurement of a dark reference frame.

Data processor 40 is any data processor which is capable of processing data from radiation measurement device 30. In a preferred embodiment, data processor 40 is a portable computer which, as will be known to those in the art, further comprising a power source. Data processor 40 may be connected to radiation measurement device 30 such as with any appropriate data communication interconnect 42, e.g. a parallel or serial cable, infrared, Bluetooth™, or the like. Software may be present in data processor 40 to perform real-time analysis of the data.

The power source may be adapted to supply power to the portable computer, radiation measurement device 30, an external device, or the like, or a combination thereof, e.g. supply power via a universal serial bus (USB) interface.

In certain embodiments, additional components 60 may be present and operatively in communication with data processor 40, e.g. a global positioning unit (GPS) and/or a data transmission device.

Figure 3:
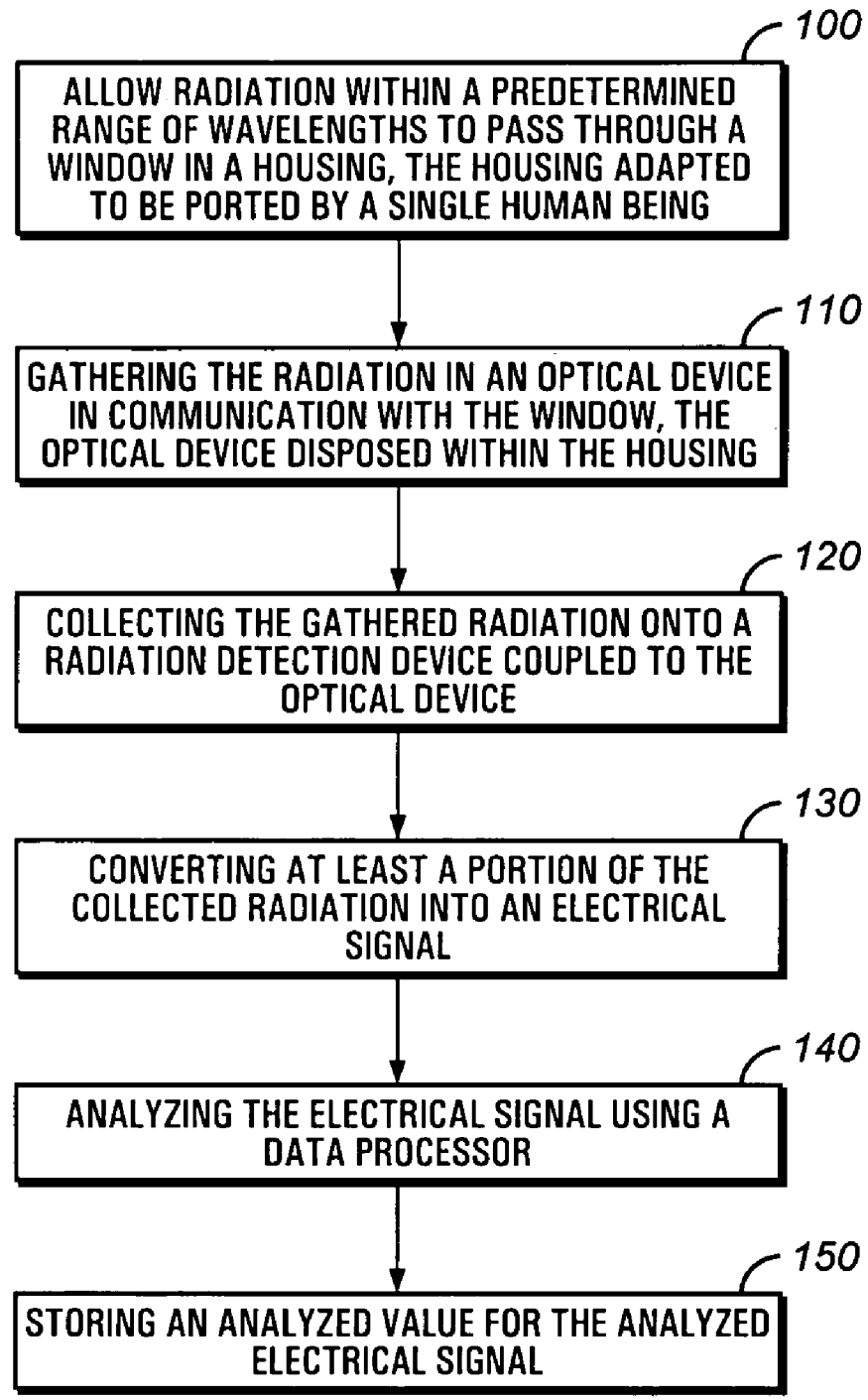
FIG. 3 is a flowchart of a first exemplary method.

In the operation of an exemplary embodiment, referring now to FIG. 3, measurement of a characteristic of radiation may be obtained using device 1 which is packaged to be transportable by a single human being. Device 1 may be used to provide a real-time display of a desired radiation spectrum, e.g. UV, as well as calculate desired characteristics of that spectrum such as spectral absorbance. Additionally, other functions may be performed, e.g. production of a scrolling plot of gas path-concentration in ppm-m, and corresponding GPS position and time. In a currently preferred embodiment, device 1 has an adjustable data acquisition rate, with generally sufficient signal to noise at a full-spectrum acquisition rate of between 300–1000 ms.

Radiation within a predetermined range of wavelengths may be allowed to pass through window 16 in housing 10, step 100. Radiation may be gathered, step 110, such as in optical device 20 which is in communication with window 16. As used herein, radiation comprises solar radiation and more especially solar radiation in the blue to ultraviolet wavelength range. Additionally, a filter may be provided to restrict available radiation to radiation within a predetermined range of wavelengths, e.g. to the blue to ultraviolet wavelength range. For example, a UV window may be used to measure downwelling scattered solar spectral radiance between 290–330 mm. If the gas of interest to be measured is $SO_2$, $SO_2$ exhibits characteristic spectral absorption features at 302.1 nm, 304.1 nm, 306.5 rim, 308.6 nm, and 310.6 nm, within the UV window filtering range. Housing 10 and the filter may also reduce the amount of stray radiation, e.g. light, reaching radiation measurement device 30.

Gathered radiation is collected onto radiation detection device 30, step 120, which coupled to optical device 20. At least a portion of the collected radiation is converted into an electrical signal, step 130, which may be analyzed using data processor 40, step 140. Converting the collected radiation further may comprise sampling the gathered radiation over the entire range of wavelengths; converting the sample into an electrical signal; and storing each sample.

Analyzing the electrical signal may further comprise analyzing two or more absorption peaks, two or more absorption troughs, or the like, or a combination of these. For example, in a currently envisioned embodiment for measuring $SO_2$ in real time, six absorption peaks and trough between 304 and 320 nm may be analyzed.

The sample may be stored, step 150, by transmitting the converted sample to data processor 40 for storage by data processor 40. Storage may be in a transient or permanent data store associated with data processor 40 or in a visual display device, e.g. one associated with data processor 40. As used herein, a visual display device comprises a screen display, a printer, or other device capable of presenting data in a human perceptible manner.

Gathered and analyzed radiation data may be used to measure path concentrations of a chosen gas of interest which exhibits detectable and measurable absorptions in these wavelengths. For example, in a preferred embodiment, analysis of one or more gas species of interest occurs in real time using data processor 40.

Figure 4:
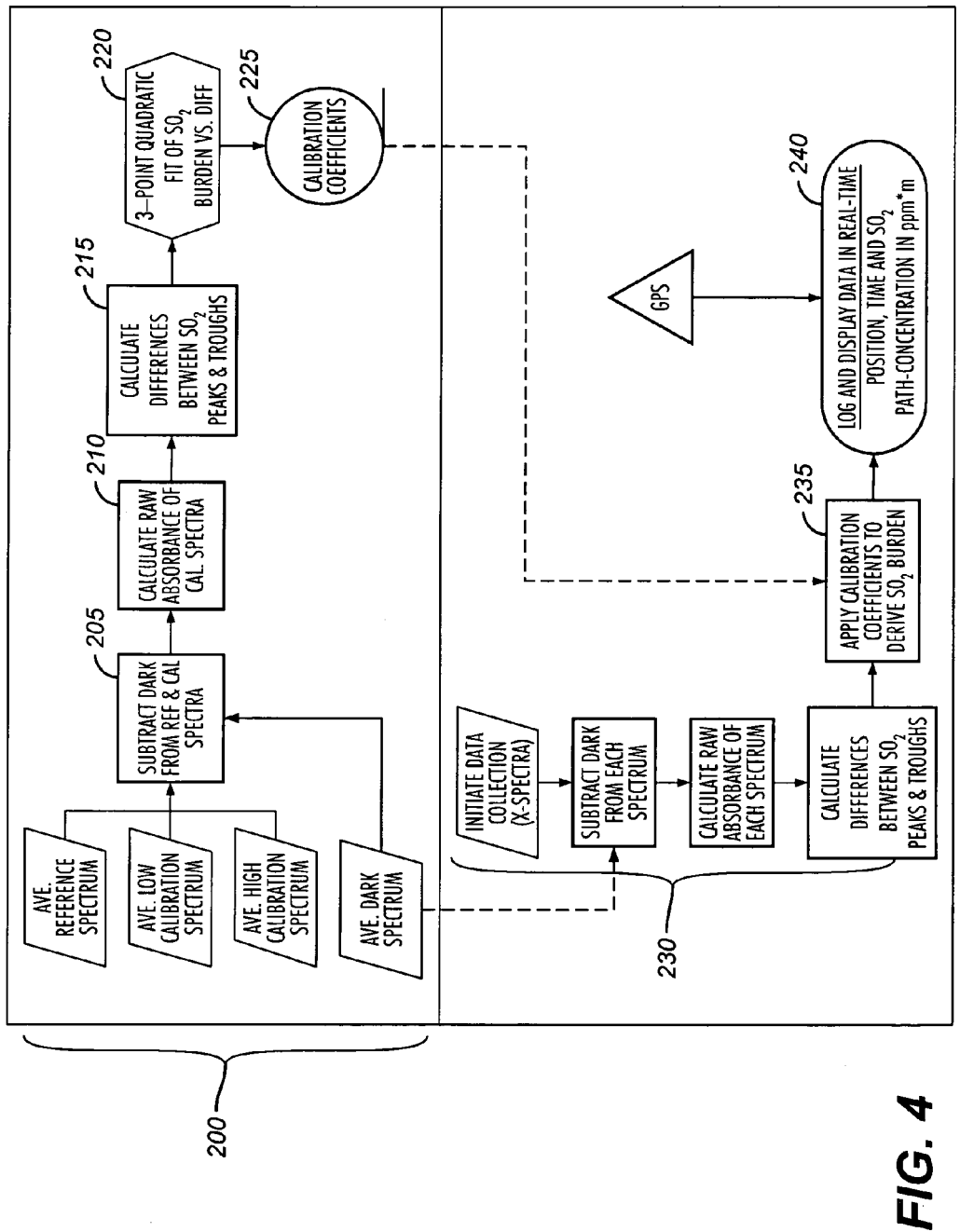
FIG. 4 is a flowchart of a second exemplary method.

In a typical use, referring now to FIG. 4, after preliminary data gathering generally illustrated at step 200, acquisition and subtraction of a dark frame, step 205, may be used to correct for dark current and electronic noise on the CCD array. To calibrate for a desired gas species path-concentration, a UV-absoring gas such as $SO_2$, a clear sky reference spectrum is collected outside of a targeted area, e.g. a gas plume from or proximate a volcano. In addition, spectra may be collected for the two (or more) calibration cells. The absorption spectrum may be calculated from:

$$A_\lambda = -\log\left(\frac{S_\lambda - D_\lambda}{R_\lambda - D\lambda}\right)$$

where $A_\lambda$ is the absorbance as a function of wavelength ($\lambda$) and $S_\lambda$, $D_\lambda$, and $R_\lambda$ are the spectral intensities of each sample, dark and references (clear sky and gas calibration), respectively Absorbance peak-trough differences at each wavelength, as a function of the path concentrations of the reference gas cells, may be manipulated to derive calibration coefficients, e.g. fit by a least squares three-point quadratic, step 215. These coefficients may then be applied to each profile spectrum deriving $SO_2$ path-concentration in real-time, steps 220–225.

This real-time comparison of reference background spectrum to measured spectra also has the benefit, that unlike some prior art devices, path-concentration results of device 1 are relatively insensitive to changes in the background cloud cover or in elevation while collecting data.

Where field conditions preclude the acquisition of fresh calibration spectra, e.g., when operating in stationary mode in the presence of $SO_2$, device 1 may employ stored calibration references. In such an environment, reference spectra may be acquired with device 1, eliminating the necessity of determining the slit function that must be convolved with laboratory reference spectra.

In typical data collection mode, derived path-concentration results (ppm-m) and corresponding GPS coordinates and time may be saved in an ASCII text format at data processor 40, e.g. step 240. These data may later be manipulated by any of several equivalent methods, e.g. using spreadsheet software. Raw spectra may be stored in a binary file to allow reprocessing of the data should that be desired.

In road-based data collection, an important part of gas flux calculations is the cosine correction for perpendicularity between the traverse segment and gas plume direction. The use of an integrated GPS allows for automation of this correction, greatly reducing postprocessing time, and increasing the quality of the data, by eliminating the requirements for strictly consistent vehicle speed and operator input. Furthermore, by assuming a normalized plume speed of 1 m/s, a velocity-normalized gas flux can be calculated upon completion of each traverse, further reducing postprocessing time.

In an exemplary use, device 1 may be used do determine gas concentrations with volcanoes. This exemplary use is presented herein not as a limitation but merely as an illustration of use.

In certain embodiments, geographical location data may be obtained, e.g. from a GPS device and a logged datum created. The logged datum may then be stored in a data store. Logged data may comprise creating an time average of analyzed values as a function of time.

A number of different operational modes can potentially be used to provide groundtruth measurements as well as base-line information on volcanic activity. The small size and weight of device 1 make it substantially easier to deploy in areas of difficult access over the prior art. The real-time integration of GPS position/time with path-concentration further allows temporal and spatial mapping of dispersed gas sources, e.g. $SO_2$, feasible.

Data may be acquired by walking traverses in and around an actively an area of interest, e.g. a degassing fumarole field. Additionally, device 1 may be deployed in stationary, tripod-mounted mode or mounted on ground-based vehicles and transported beneath gas plumes. Multiple devices 1 may be deployed as a ground-based array near the gas source to measure the instantaneous spatial distribution of the column abundance of a plume. These data may potentially be used for analyzing vent degassing and plume dispersion behavior. The incorporation of solid-state microprocessors and dataloggers along with wireless telemetry to remote continuous monitoring systems greatly facilitates this.

In the art, the largest source of uncertainty is caused by difficulties in accurately measuring the wind speed, which is used as a proxy for the plume velocity vector. Device 1 may use a ground-based method using multiple devices 1 to directly measure plume speed by correlating the path-concentration signal from each unit and determining the time offset.

It will be understood that various changes in the details, materials, and arrangements of the parts which have been described and illustrated above in order to explain the nature of this invention may be made by those skilled in the art without departing from the principle and scope of the invention as recited in the appended claims.

We claim:

1. A device for analyzing a gas, comprising:
   a. a housing adapted to be carried by a single human being;
   b. optics, responsive to a known range of ultraviolet radiation, disposed at least partially within the housing;
   c. a radiation measurement device disposed at least partially within the housing and operatively in communication with the optics;
   d. a non-database calibration spectrum source; and
   e. a data processor operatively in communication with the radiation measurement device.

2. The device according to claim 1, wherein the housing further comprises:
   a. a shell comprising a durable material, the shell comprising an exterior, a surface and an interior; and
   b. a padding disposed within the interior of the shell, the padding adapted to shield components disposed within the interior from at least one of (i) physical shock or (ii) environmental hazards.

3. The device according to claim 1, wherein the housing further comprises a window at least partially defining a field of view for a telescope.

4. The device according to claim 3, wherein the optics further comprise:
   a. a mirror disposed in a pathway for radiation entering the window; and
   b. a diffraction grating disposed intermediate the mirror and the radiation measurement device.

5. The device according to claim 1, wherein the window further comprises a band-pass material for a predetermined wave length range of ultraviolet radiation.

6. The device according to claim 1, wherein the optics further comprises a fiber optic collimating lens directly coupled to an input aperture of the radiation measurement device.

7. The device of claim 1, wherein the radiation measurement device further comprises a charge coupled device responsive to wave lengths of a predetermined ultraviolet range.

8. The device according to claim 1, wherein the radiation measurement device comprises a spectrometer.

9. The device according to claim 8, wherein the data processor comprises a portable computer, the portable computer further comprising a power source adapted to supply power to at least one of (i) the portable computer, (ii) the radiation measurement device, or (iii) an external device.

10. The device of claim 1, further comprising a calibration cell disposed at least partially within the housing and operatively in communication with the radiation measurement device.

11. The device of claim 10 wherein the calibration cell further comprises:
    a. a high calibration cell having a known concentration of calibrating material; and
    b. a low calibration cell having a known concentration of calibrating material.

12. The device according to claim 1, further comprising a global positioning unit (GPS) operatively in communication with the data processor.

13. A method of obtaining a measurement of a characteristic of radiation, comprising:
    a. allowing radiation within a predetermined range of ultraviolet wavelengths to pass through a window in a housing, the housing adapted to be carried by a single human being;
    b. acquiring a current predetermined calibration spectrum substantially concurrently with obtain current measurements without use of stored data;
    c. gathering the radiation in an optical device in communication with the window, the optical device disposed within the housing;
    d. collecting the gathered radiation onto a radiation detection device coupled to the optical device;
    e. converting at least a portion of the collected radiation into an electrical signal;

f. analying the electrical signal using a data processor;

g. storing an analyzed value for the analyzed electrical signal.

14. The method of claim 13, further comprising:

a. providing a filter to restrict available radiation to radiation within a predetermined range of wavelengths.

15. The method of claim 13, wherein the predetermined range of ultraviolet wavelengths extend down to a predetermined blue wavelenth, further comprising:

a. using atmospherically scattered solar radiation in the blue to ultraviolet wavelength range as a source to measure path-concentrations of a chosen gas of interest which exhibits detectable and measurable absorptions in these wavelengths.

16. The method of claim 13, wherein converting the collected radiation further comprises:

a. sampling the gathered radiation over the entire range of wavelengths;

b. converting the sample into an electrical signal; and c. storing each sample.

17. The method of claim 13, wherein analyzing the electrical signal further comprises analyzing at least one of (i) more than two absorption peaks in the ultraviolet range or (ii) more than two absorption troughs in the ultraviolet range.

18. The method of claim 13, wherein analyzing the electrical signal is accomplished in real time.

19. The method of claim 18, wherein creating logged data further comprises creating an time average of analyzed values as a function of time.

20. The method of claim 13, wherein the analyzed value is stored in at least one of (i) a visual display device, (ii) a transient data store, or (iii) a permanent data store.

21. The method of claim 13, further comprising:

a. obtaining geophysical location data from a GPS device;

b. creating logged data using the geophysical location data; and c. storing the logged data in a data store.

22. The method of claim 13, wherein acquiring a calibration spectrum further comprises:

a. rotating a calibration cell of a known concentration into the path of radiation;

b. allowing radiation to pass through the calibration cell to the optical device; and c. adjusting the analyzed value to correspond to the known concentration of the calibration cell without using a stored data source.

23. The method of claim 13, further comprising initializing an analyzed value, comprising:

a. obtaining a measurement of a calibration cell;

b. obtaining a measurement of clean air; and c. obtaining measurement of a dark reference frame.

* * * * *